(12) United States Patent
Iijima

(10) Patent No.: US 9,962,137 B2
(45) Date of Patent: May 8, 2018

(54) CONTROL APPARATUS, RADIATION IMAGING APPARATUS, RADIATION IMAGING SYSTEM, AND CONTROL METHOD OF RADIATION IMAGING APPARATUS, CONTROLLING A STATE OF A RADIATION SENSOR BASED ON FIRST AND SECOND TIMES FROM AN INITIALIZATION OPERATION

(71) Applicant: CANON KABUSHIKI KAISHA, Tokyo (JP)

(72) Inventor: Tadahiko Iijima, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 287 days.

(21) Appl. No.: 14/192,972

(22) Filed: Feb. 28, 2014

(65) Prior Publication Data
US 2014/0252206 A1 Sep. 11, 2014

(30) Foreign Application Priority Data

Mar. 6, 2013 (JP) ................................ 2013-044720

(51) Int. Cl.
*G01T 1/16* (2006.01)
*A61B 6/00* (2006.01)
(52) U.S. Cl.
CPC .............. *A61B 6/54* (2013.01); *A61B 6/4233* (2013.01); *A61B 6/465* (2013.01)

(58) Field of Classification Search
CPC ......... A61B 6/54; A61B 6/4233; A61B 6/465; A61B 6/548; A61B 6/542; H04N 5/325; G01T 1/16; G01T 1/2018
USPC .... 250/208.1, 214 R, 214.1, 370.09; 378/37, 378/62, 91, 98.7, 114
See application file for complete search history.

(56) References Cited

U.S. PATENT DOCUMENTS

2013/0279656 A1   10/2013   Iijima .............................. 378/62

FOREIGN PATENT DOCUMENTS

JP      2009-219538      10/2009
JP      2010-124025      6/2010
JP      2010-273858      12/2010

*Primary Examiner* — Que T Le
(74) *Attorney, Agent, or Firm* — Fitzpatrick Cella Harper and Scinto

(57) ABSTRACT

A control apparatus for a radiation sensor, including pixels each for obtaining electric charges, includes: a control unit configured to start driving for imaging in response to radiation irradiation, and stop the driving when a first time elapses after the start of the driving; and a receiving unit configured to externally receive a predetermined instruction signal. The control unit is configured to, in response to reception of the predetermined instruction signal, control a state of the radiation sensor based on a difference between the first time and a second time from the start of the driving to the reception of the predetermined instruction signal.

20 Claims, 7 Drawing Sheets

IDLE STATE SCREEN

IMAGING PREPARATION STATE SCREEN 1

IMAGING ENABLE STATE SCREEN

IMAGING PREPARATION STATE SCREEN 2

IMAGING STATE SCREEN

CONTROL APPARATUS, RADIATION IMAGING APPARATUS, RADIATION IMAGING SYSTEM, AND CONTROL METHOD OF RADIATION IMAGING APPARATUS, CONTROLLING A STATE OF A RADIATION SENSOR BASED ON FIRST AND SECOND TIMES FROM AN INITIALIZATION OPERATION

BACKGROUND OF THE INVENTION

Field of the Invention

The present invention relates to a control apparatus, a radiation imaging apparatus, a radiation imaging system, a control method of the radiation imaging apparatus, and a storage medium.

Description of the Related Art

There has been commercially available a radiation imaging system using a radiation generating apparatus for irradiating an object with radiation, a radiation imaging apparatus for generating a clear radiation image by performing image processing for a radiation image obtained by digitizing a radiation image which is the intensity distribution of radiation, and an image processing apparatus. Such a radiation imaging system transfers, to the image processing apparatus such as a control computer for image processing and storage, radiation image data obtained by the radiation imaging apparatus upon causing the radiation generating apparatus to irradiate an object with radiation. The image processing apparatus displays an image having undergone image processing on a display device such as a display.

The radiation imaging apparatus is formed by stacking a scintillator on a photoelectric conversion device (conversion device) for converting radiation into an image signal electric charge (an electric signal), and the like. The radiation imaging apparatus converts radiation into visible light through the scintillator, holds the visible light as electric charges, and forms an image from the amount of readout electric charges. The radiation imaging apparatus which forms an image from the amount of electric charges requires a lapse of a given time after energization of a circuit for driving the conversion device to enter an imaging enable state for image quality stabilization.

For example, Japanese Patent Laid-Open No. 2010-273858 discloses a method of saving power by shortening the time to enable imaging. To shorten the time to enable imaging, Japanese Patent Laid-Open No. 2010-273858 proposes a method of changing the timeout time after energization of a circuit for setting an imaging enable state, in accordance with the input state of patient information and an imaging protocol.

In a conventional radiation imaging system, the timing of radiation generation by a radiation generating apparatus is synchronized with the timing of imaging by a radiation imaging apparatus by performing communication between the radiation generating apparatus and the radiation imaging apparatus, and then the radiation imaging apparatus performs imaging. Recently, however, as disclosed in Japanese Patent Laid-Open No. 2009-219538, to simplify a system arrangement required for communication, a radiation imaging system which adopts a scheme of performing imaging immediately after detection of radiation in the radiation imaging apparatus without performing communication between a radiation generating apparatus and a radiation imaging apparatus has been developed. In this radiation imaging system, if an attempt is made to ensure a wide dynamic range which covers from a low radiation dose to a high radiation dose, a circuit for driving a conversion device or another electric circuit element unwantedly generates noise such as thermal noise and shot noise. Therefore, the S/N ratio decreases especially in a low-radiation-dose region, thereby deteriorating the image quality of an obtained radiation image. If a sensor is set in an imaging enable state for a given time or longer, the influence of noise becomes large. For this reason, noise is reduced by stopping driving of the sensor to set an imaging disable state (sleep mode) and to reset electric charges accumulated in the conversion device, thereby suppressing deterioration in image quality.

According to the method described in Japanese Patent Laid-Open No. 2010-273858, if it takes time to input patient information and an imaging protocol, the remaining time for actual imaging shortens. For example, timeout may occur during adjustment of the respiratory timing of a patient, resulting in an imaging disable state. This requires a given waiting time to set an imaging enable state again.

In addition, according to Japanese Patent Laid-Open No. 2009-219538, if radiation irradiation is performed without noticing that driving of the sensor stops to set an imaging disable state, desired radiation imaging may fail (misshooting).

SUMMARY OF THE INVENTION

The present invention has been made in consideration of the above problems, and provides a radiation imaging technique which can control the operating state of an apparatus according to the result of determining whether a remaining imaging enable time is equal to or longer than a threshold time.

According to one aspect of the present invention, there is provided a control apparatus for a radiation sensor, including pixels each for obtaining electric charges, comprising: a control unit configured to start driving for imaging in response to radiation irradiation, and stop the driving when a first time elapses after the start of the driving; and a receiving unit configured to externally receive a predetermined instruction signal, wherein the control unit is configured to, in response to reception of the predetermined instruction signal, control a state of the radiation sensor based on a difference between the first time and a second time from the start of the driving to the reception of the predetermined instruction signal.

According to the present invention, it is possible to control the operating state of an apparatus according to the result of determining whether a remaining imaging enable time is equal to or longer than a threshold time. This makes it possible to perform imaging while ensuring a sufficient imaging time in imaging, thereby preventing desired radiation imaging from failing.

Further features of the present invention will become apparent from the following description of exemplary embodiments (with reference to the attached drawings).

DESCRIPTION OF THE EMBODIMENTS

Embodiments of the present invention will be exemplarily described in detail below with reference to the accompanying drawings. Note that the constituent elements described in the embodiments are merely examples. The technical scope of the present invention is determined by the scope of claims and is not limited by the following individual embodiments.

First Embodiment

Figure 1:
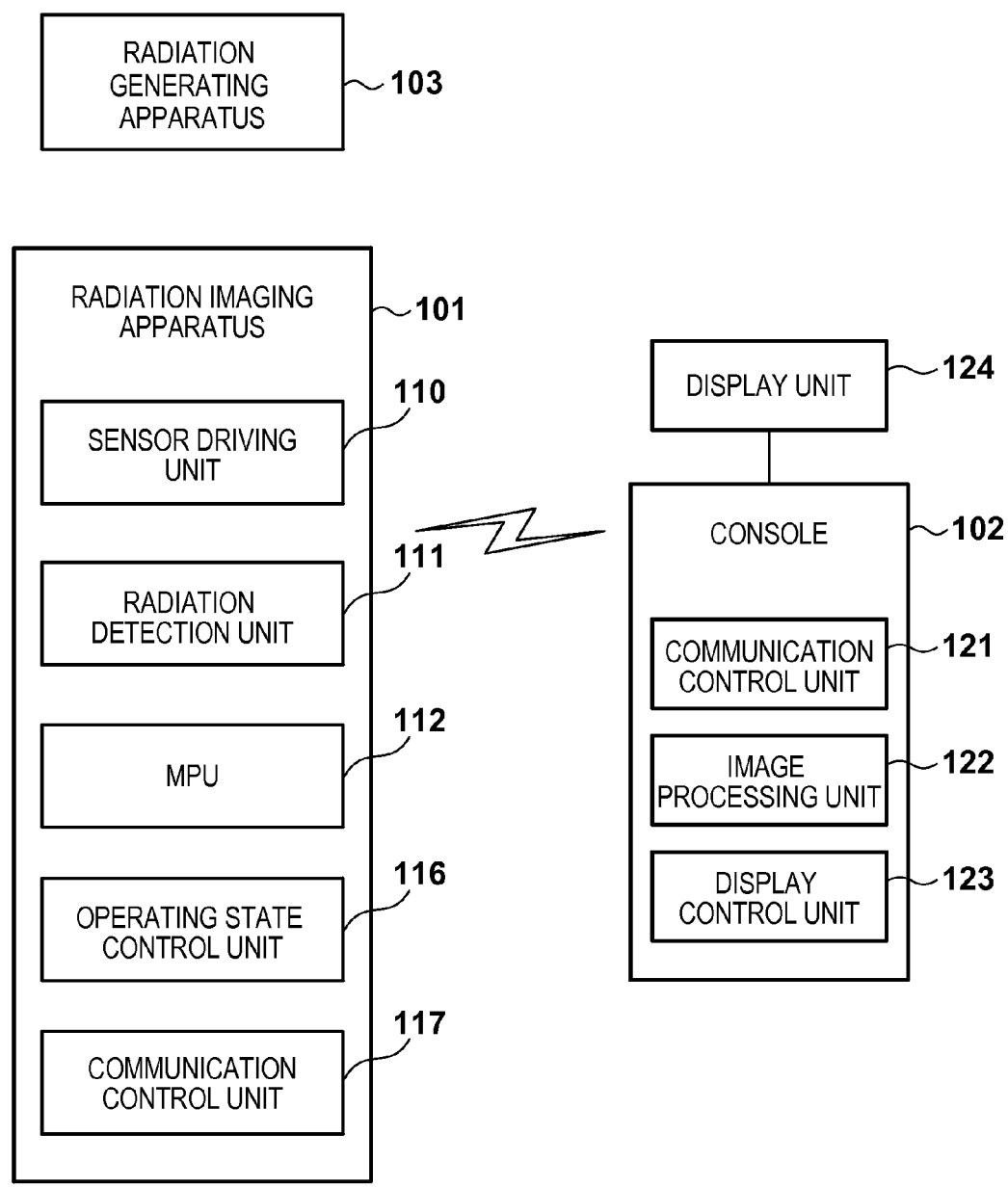
FIG. 1 is a block diagram showing an example of the arrangement of a radiation imaging system according to an embodiment.

FIG. 1 is a block diagram showing an example of the arrangement of a radiation imaging system according to an embodiment of the present invention. The radiation imaging system includes a radiation imaging apparatus 101, a console 102 (information processing apparatus) for controlling the radiation imaging apparatus 101, and a radiation generating apparatus 103 for irradiating an object with radiation.

The radiation imaging apparatus 101 includes a sensor driving unit 110, a radiation detection unit 111, an MPU 112, an operating state control unit 116, and a communication control unit 117.

The radiation detection unit 111 detects radiation from the radiation generating apparatus 103. For example, the radiation detection unit 111 includes a sensor array having a two-dimensional array of pixels, each constituted by a conversion device for converting radiation into an image signal electric charge (electric signal) and a switching element such as a TFT for transferring an electric signal to the outside. The sensor driving unit 110 drives the radiation detection unit 111. The MPU 112 functions as a control unit for controlling the overall operation of the sensor driving unit 110, radiation detection unit 111, and radiation imaging apparatus 101.

The radiation imaging apparatus 101 includes the operating state control unit 116 for controlling the operating state of the radiation imaging apparatus 101 by switching energization of the MPU 112, the sensor driving unit 110, and the radiation detection unit 111. The radiation imaging apparatus 101 also includes the communication control unit 117 for controlling communication with the console 102.

A communication control unit 121 of the console 102 can perform data communication between the radiation imaging apparatus 101 and the console 102, such as reception of a captured image transferred from the radiation imaging apparatus 101.

An image processing unit 122 of the console 102 performs image processing for converting the captured image received from the radiation imaging apparatus 101 into an image suitable for diagnosis. Based on the captured image data transmitted to the console 102, a display control unit 123 of the console 102 performs display control for displaying an image based on electric charges read out from the radiation detection unit 111, an operation UI, and the like on a display unit 124.

Wireless LAN communication can be used for data communication between the communication control unit 121 of the console 102 and the communication control unit 117 of the radiation imaging apparatus 101. For example, the communication control unit of the console 102 has a wireless adapter and an access point function implemented by software. If the radiation imaging apparatus 101 serves as a wireless LAN child device and the console 102 serves as a wireless LAN parent device, the console 102 can connect to the radiation imaging apparatus 101 by wireless LAN communication. Note that data communication is not limited to wireless LAN communication, and may be wireless communication using another scheme or wired communication using a cable.

In the sensor array of the radiation detection unit 111, a plurality of conversion devices each for converting radiation into an electric charge are arranged along a scan line. For example, the sensor array is formed by arranging a two-dimensional array of pixels, each of which includes a photoelectric conversion device (radiation detection device) and a switching element such as a TFT. For example, a scintillator is provided on each pixel. Radiation emitted from the radiation generating apparatus 103 is converted into visible light through the scintillator, and the converted visible light enters the photoelectric conversion device of each pixel. The photoelectric conversion device generates electric charges according to the visible light. The scope of the present invention is not limited to this arrangement example. For example, it is possible to use a so-called direct conversion type conversion device which directly converts incident radiation into electric charges without providing any scintillator.

The radiation imaging apparatus 101 accumulates electric charges and reads out the electric charges by switching ON/OFF of the TFTs, thereby obtaining a radiation image. The radiation imaging apparatus 101 causes the radiation detection unit 111 to detect radiation generated by the radiation generating apparatus 103, reads out electric charges accumulated in the sensor array, forms radiation image data, and transmits the radiation image data to the console 102.

The radiation imaging apparatus 101 includes four operating states, that is, an idle state, an imaging preparation state, an imaging enable state, and an imaging state. The operating state control unit 116 controls the operating state of the radiation imaging apparatus 101 by switching energization of the MPU 112, the sensor driving unit 110, and the radiation detection unit 111. The operating state control unit 116 executes driving to start imaging in response to radiation irradiation, and stops the driving when a first time t1 elapses after the start of the driving. The communication control unit 117 externally receives a predetermined instruction signal. The operating state control unit 116 and the communication control unit 117 can function as a control apparatus for the radiation detection unit (radiation sensor) in which a plurality of pixels each for obtaining electric charges by radiation irradiation are arranged. In response to reception of the predetermined instruction signal, the operating state control unit 116 controls the state of the radiation detection unit (radiation sensor) based on the difference between the first time and a second time t2 ($<$t1) from the start of execution of the driving until the predetermined instruction signal is received.

In the idle state, the operating state control unit 116 controls the operating state of the radiation imaging apparatus 101 so as to energize the MPU 112 and stop energization of the sensor driving unit 110 and radiation detection unit 111. In this idle state, the radiation imaging apparatus 101 cannot perform imaging (imaging disable state). In the idle state, the electric charges accumulated in the sensor array of the radiation detection unit 111 are reset (initialization processing). Resetting the accumulated electric charges can suppress deterioration in image quality due to the influence of noise.

In the imaging preparation state, the operating state control unit 116 controls the operating state of the radiation imaging apparatus 101 so as to energize the MPU 112 and the sensor driving unit 110 and not to energize the radiation detection unit 111. In the imaging preparation state, the radiation detection unit 111 is not energized and hence cannot detect the radiation from the radiation generating apparatus 103. Therefore, the radiation imaging apparatus 101 cannot perform imaging (imaging disable state). In the imaging preparation state, the console 102 can be used to, for example, refer to an image (past image) transmitted by the radiation imaging apparatus 101 in the past, and perform processing of making an annotation on the past image.

Although the operating state can quickly transit from the imaging preparation state to the imaging enable state, a given transition time (for example, about 10 sec) needs to elapse between the idle state and the imaging preparation state for image quality stabilization. Since the user highly probably performs imaging thereafter, it is desirable to perform, if possible, an operation such as referring to past images in the imaging preparation state in order to shorten the waiting time in imaging. While the user performs an operation such as referring to past images in the imaging enable state, the radiation detection unit 111 is energized even though imaging is not performed. Such operation is therefore undesirable in terms of power saving.

In the imaging enable state, the operating state control unit 116 controls to energize the MPU 112, the sensor driving unit 110, and the radiation detection unit 111 to enable the respective units to operate. The sensor driving unit 110 drives the radiation detection unit 111. The radiation detection unit 111 detects the radiation generated by the radiation generating apparatus 103 and enters the imaging enable state. In the imaging enable state, the radiation detection unit 111 is energized, and thus the power consumption is higher than that in the imaging preparation state.

In the imaging state, the sensor driving unit 110 drives the radiation detection unit 111 under the overall control of the MPU 112, thereby accumulating electric charges in the respective conversion devices of the sensor array of the radiation detection unit 111. The radiation imaging apparatus 101 reads out the electric charges accumulated in the respective conversion devices of the sensor array of the radiation detection unit 111 and forms radiation image data.

Figure 4:
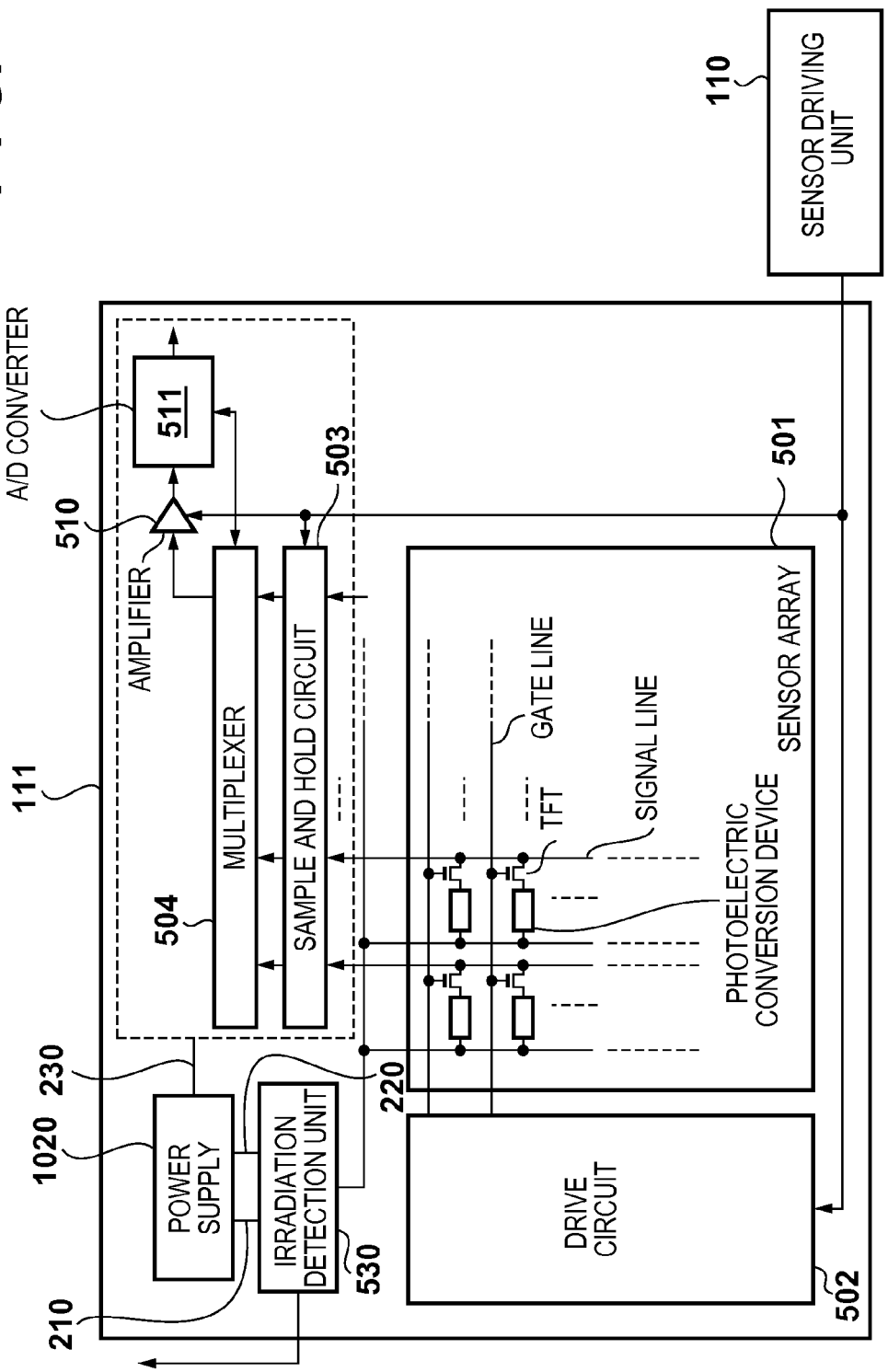
FIG. 4 is a circuit diagram showing an example of the arrangement of a radiation detection unit.

FIG. 4 is a circuit diagram showing an example of the arrangement of the radiation detection unit 111. A drive circuit 502 simultaneously addresses all the pixels on the rows on a sensor array 501, which are two-dimensionally arranged. After that, electric charges (pixel outputs) of the respective pixels held by a sample and hold circuit 503 are sequentially read out via a multiplexer 504 and amplified by an amplifier 510. An A/D converter 511 converts the resultant electric charges into digital image data. Every time scanning on each row is complete, the drive circuit 502 sequentially drives and scans the respective subsequent rows on the sensor array 501 to finally convert the electric charges output from all the pixels into digital values. This makes it possible to read out the radiation image data. In this case, the apparatus performs scanning while a voltage applied to each column signal line connected to a corresponding one of the pixels on each row is fixed to a specific value, and discards obtained electric charges to discharge dark electric charges, thereby discharging (resetting) the dark electric charges accumulated in the respective pixels. This completes the initialization of the sensor array 501. The sensor driving unit 110 controls driving of the radiation detection unit 111, a readout operation, and the like.

If the image data converted by the A/D converter 511 is radiation image data obtained by radiation irradiation, offset correction is performed to subtract, from the radiation image data, offset image data obtained from only the dark electric charge components in the respective pixels. By performing offset correction, it is possible to obtain a captured image from which unnecessary dark electric charge components have been removed.

An irradiation detection unit 530 detects the start of radiation irradiation. A power supply 1020 supplies power for driving the irradiation detection unit 530 via a wiring 210. In addition, the power supply 1020 supplies power for driving a sensor (the sensor array 501 and the drive circuit 502) via a wiring 220. Furthermore, the power supply 1020 supplies power for driving an amplifier (the sample and hold circuit 503, the multiplexer 504, the A/D converter 511, and the amplifier 510) via a wiring 230.

The operating state control unit 116 controls the timings of supplying power from the power supply 1020 to the irradiation detection unit 530, the sensor, and the amplifier and the timings of stopping supplying power to them. The operating state control unit 116 can switch (ON/OFF) the operating states of the irradiation detection unit 530, sensor, and amplifier by controlling the timings of supplying power.

Figure 2:
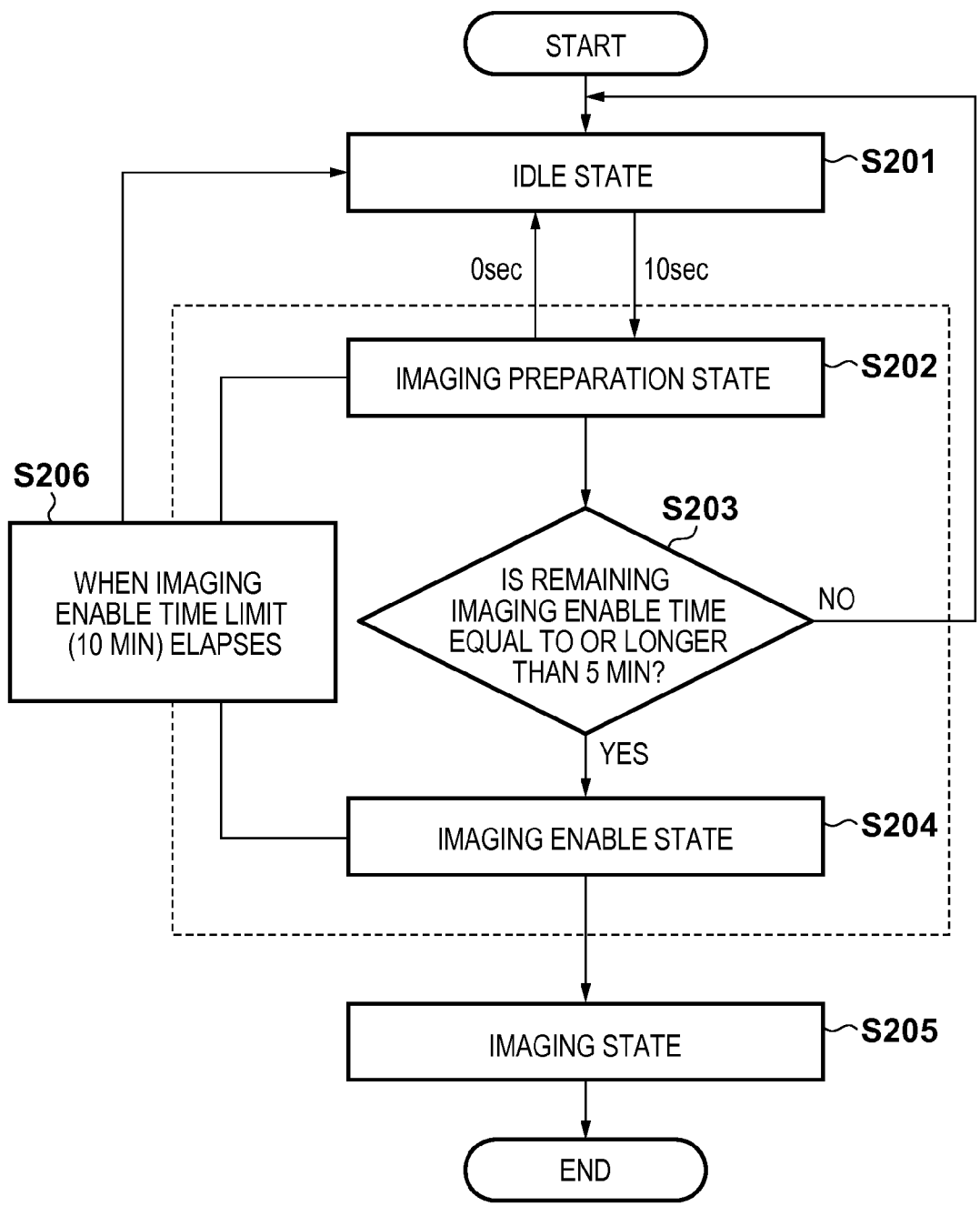
FIG. 2 is a flowchart for explaining the operation procedure of a radiation imaging apparatus according to the first embodiment.

FIG. 2 is a flowchart for explaining the operation procedure of the radiation imaging apparatus according to the first embodiment of the present invention.

In step S201, the radiation imaging apparatus 101 is in the idle state. For example, in response to reception of an operation input from the console 102, the operating state control unit 116 of the radiation imaging apparatus 101 controls energization so as to transit from the idle state to the imaging preparation state (step S202). In the idle state, the MPU 112 is energized. Upon transiting to the imaging preparation state, the operating state control unit 116 controls to energize the MPU 112 and the sensor driving unit 110.

To transit from the idle state to the imaging preparation state, a predetermined transition time is needed. As the transition time, for example, 10 sec is needed. Note that the transition time is merely an example, and the scope of the present invention is not limited to this. It is possible to quickly transit from the imaging preparation state to the idle state without requiring a predetermined transition time.

In step S202, the operating state control unit 116 energizes the sensor driving unit 110 to operate, thereby initializing the sensor array of the radiation detection unit 111.

Note that a time after the initialization of the sensor array, during which imaging of a radiation image can be performed using the radiation detection unit 111, is defined as an "imaging enable time limit". During the imaging enable time limit, the radiation detection unit 111 can continuously perform imaging while maintaining the imaging ability without any influence of noise. An elapsed time after the start of the use of the radiation detection unit 111 is defined as an "elapsed imaging enable time". Furthermore, a time obtained by subtracting the "elapsed imaging enable time" from the "imaging enable time limit" (subtraction processing) is defined as a "remaining imaging enable time".

If the imaging enable time limit is, for example, 10 minutes, the total time from initialization during which the apparatus is in the imaging preparation state (step S202) or the imaging enable state (step S204) is limited to 10 min minutes. For example, the operating state control unit 116 measures an elapsed time using a timer. If the imaging enable time limit elapses in step S202 or S204, the operating state control unit 116 controls energization of the respective units of the radiation imaging apparatus 101 so as to transit to the idle state (step S201) (step S206).

When the operating state is caused to transit from the imaging preparation state to the imaging enable state, the operating state control unit 116 determines in step S203 whether the remaining imaging enable time is equal to or longer than a threshold time (for example, 5 min) indicating that imaging is possible without any influence of deterioration in image quality due to noise. If it is determined in step S203 that the remaining imaging enable time is shorter than the threshold time (NO in step S203), the process returns to step S201, and the operating state control unit 116 controls energization of the respective units of the radiation imaging apparatus 101 so as to transit to the idle state (step S201).

If it is determined in step S203 that the remaining imaging enable time is equal to or longer than the threshold time (YES in step S203), the process advances to step S204, and the operating state control unit 116 controls energization of the respective units of the radiation imaging apparatus 101 so as to transit to the imaging enable state. Note that 5 min set as the threshold time indicating that imaging is possible is merely an example, and the scope of the present invention is not limited to this.

If the process advances to step S204 according to the determination in step S203, it is ensured that the remaining imaging enable time is equal to or longer than the threshold time indicating that imaging is possible without any influence of deterioration in image quality due to noise. It is, therefore, possible to ensure a sufficient time required for imaging such as adjustment of the state of a subject, for example, adjustment of the respiratory timing of a subject. If it is determined in step S203 that the remaining imaging enable time is shorter than the threshold time, the process returns to step S201 to transit to the idle state. After a predetermined transition time (for example, 10 sec) elapses, the apparatus enters the imaging preparation state in step S202, and determination of the remaining imaging enable time is made in step S203. If it is determined in step S203 that the remaining imaging enable time is equal to or longer than the threshold time, the process advances to step S204 and the operating state control unit 116 controls energization of the respective units of the radiation imaging apparatus 101 so as to transit to the imaging enable state (step S204). That is, the operating state control unit 116 controls to energize the MPU 112, the sensor driving unit 110, and the radiation detection unit 111 to enable the respective units to operate.

In step S205, the sensor driving unit 110 drives the radiation detection unit 111 under the overall control of the MPU 112, thereby accumulating electric charges in the respective conversion devices of the sensor array of the radiation detection unit 111. The radiation imaging apparatus 101 reads out the electric charges accumulated in the respective conversion devices of the sensor array of the radiation detection unit 111 and forms radiation image data. The radiation imaging of the subject then ends.

Second Embodiment

Figure 3:
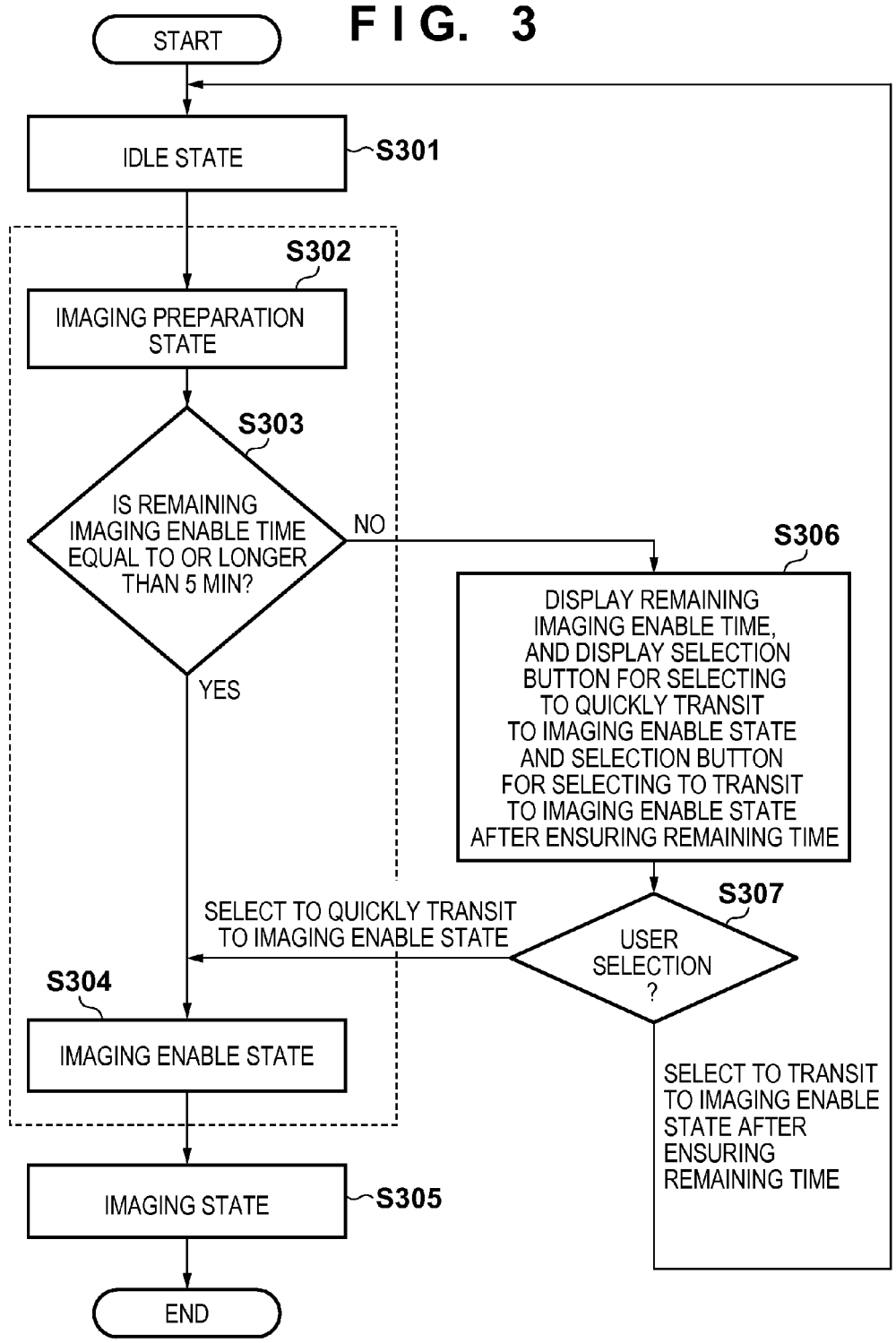
FIG. 3 is a flowchart for explaining the operation procedure of a radiation imaging apparatus according to the second embodiment.

The operation procedure of a radiation imaging apparatus according to the second embodiment of the present invention will be described with reference to a flowchart shown in FIG. 3. Depending on an imaging technique, it may be possible to complete imaging in a short time. In this case, quickly transiting to the imaging enable state may be more efficient than returning to the idle state to transit to the imaging enable state through the imaging preparation state. In this embodiment, an arrangement in which when the remaining imaging enable time is shorter than a threshold time, the user can select whether to quickly transit to the imaging enable state or return to the idle state to transit to the imaging enable state through the imaging preparation state will be described.

The arrangement of a radiation imaging apparatus 101 and that of a radiation imaging system using the radiation imaging apparatus 101 are the same as those exemplified in the first embodiment and a repetitive description will be omitted.

In step S301, the radiation imaging apparatus 101 is in the idle state. For example, in response to reception of an operation input from a console 102, an operating state control unit 116 of the radiation imaging apparatus 101 controls energization so as to transit from the idle state to the imaging preparation state (step S302). To transit from the idle state (step S301) to the imaging preparation state (step S302) shown in FIG. 5 (to be described later), a given transition time (for example, about 10 sec) needs to elapse for stabilization of the state of a sensor (an image stabilization waiting state). The state of waiting for the transition time to elapse is referred to as an image stabilization waiting state. Note that the transition time is merely an example and the scope of the present invention is not limited to this.

When the operating state is caused to transit from the imaging preparation state (step S302) to the imaging enable state (step S304), the operating state control unit 116 determines in step S303 whether the remaining imaging enable time is equal to or longer than a threshold time (for example, 5 min) indicating that imaging is possible. If it is determined in step S303 that the remaining imaging enable state is shorter than the threshold time (NO in step S303), the process advances to step S306.

In step S306, the operating state control unit 116 outputs information indicating the remaining imaging enable time. A communication control unit 117 of the radiation imaging apparatus 101 communicates with a communication control unit 121 of the console 102 by wireless communication or wired communication, and transmits the information indicating the remaining imaging enable time to the console 102.

A display control unit 123 of the console 102 displays the received information indicating the remaining imaging enable time on a display unit 124. The display control unit 123 displays, on the display unit 124, the information indicating the remaining imaging enable time, an instruction button for selecting to transit to the imaging enable state (step S304) after ensuring the remaining imaging enable time equal to or longer than the threshold time, and an instruction button for selecting to quickly transit to the imaging enable state. The user (operator) can confirm display of the display unit 124, and select whether to transit to the imaging enable state (step S304) after ensuring the remaining imaging enable time equal to or longer than the threshold time or quickly transit to the imaging enable state. The selection input of the user (operator) is transmitted to the operating state control unit 116 via the communication control unit 121 of the console 102 and the communication control unit 117 of the radiation imaging apparatus 101. The operating state control unit 116 controls the operating state of the radiation imaging apparatus 101 according to the received selection input of the user (operator).

If it is determined in step S307 that transiting to the imaging enable state after ensuring the remaining imaging enable time equal to or longer than the threshold time has been selected, the process returns to step S301, and thereafter the same processing is repeated. If it is determined in step S303 that the remaining imaging enable time is equal to or longer than the threshold time (YES in step S303), the process advances to step S304, and the operating state of the radiation imaging apparatus 101 transits from the imaging preparation state (step S302) to the imaging enable state (step S304).

On the other hand, if it is determined in step S307 that quickly transiting to the imaging enable state has been selected, the operating state control unit 116 causes the operating state of the radiation imaging apparatus 101 to quickly transit to the imaging enable state (step S304). Depending on an imaging technique applied to a subject, it may be possible to complete imaging in a short time. According to the arrangement of the embodiment, when the remaining imaging enable time is shorter than the threshold time, the user can select whether to quickly transit to the imaging enable state or return to the idle state to transit to the imaging enable state through the imaging preparation state. It is possible to perform imaging more efficiently depending on an imaging technique. The arrangement in which the instruction buttons (user interface) for selecting whether to transit to the imaging enable state after ensuring the remaining imaging enable time equal to or longer than the threshold time or quickly transit to the imaging enable state are displayed on the display unit 124 connected to the console 102 has been explained with reference to FIG. 3. The scope of the present invention is not limited to this example. For example, the display control unit 123 may be provided in the radiation imaging apparatus 101 and the display unit 124 may be connected to the radiation imaging apparatus 101.

The selection in step S307 is not limited to selection via the instruction button (user interface), and selection can be accepted using another method. Furthermore, a case in which the user makes a selection in step S307 has been described. It is, however, possible to determine in advance a procedure to be used according to a specific imaging technique or user, and execute processing according to the procedure determined in advance. For example, if imaging technique A is set, the operating state returns to the idle state, and transits to the imaging enable state through the imaging preparation state. Alternatively, if imaging technique B is set, the operating state quickly transits to the imaging enable state. In this way, it is possible to determine a processing procedure in advance, and switch the processing procedure according to imaging conditions.

Figure 5:
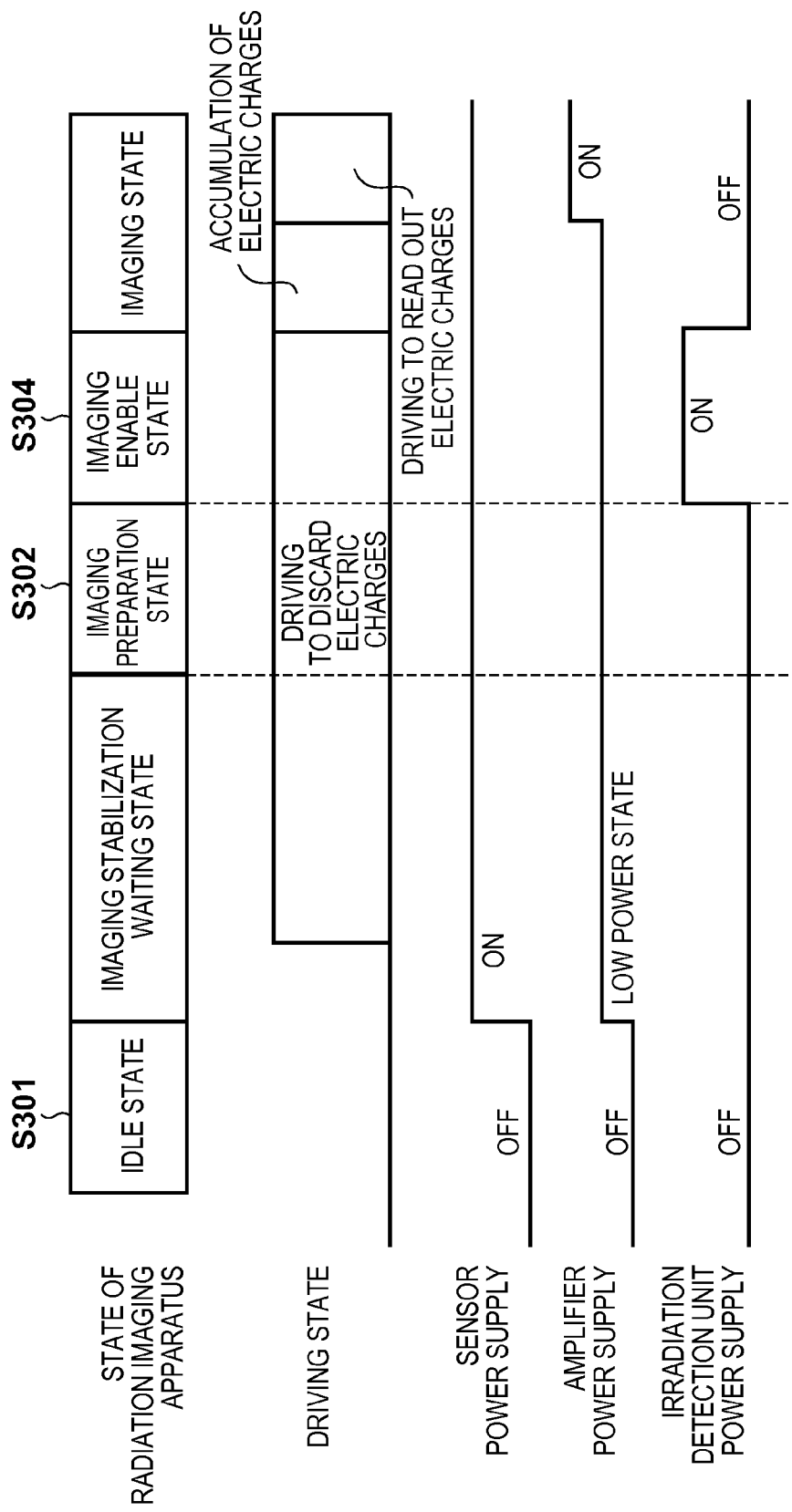
FIG. 5 is a view showing the relationship between the operating state of the radiation imaging apparatus, the driving state of a sensor array, and the power supply states of respective units of the radiation detection unit.

FIG. 5 is a view showing the relationship between the operating state of the radiation imaging apparatus 101, the driving state of a sensor array 501 of a radiation detection unit 111, and the power supply states of respective units (a sensor, an amplifier, and an irradiation detection unit 530) of the radiation detection unit 111. Referring to FIG. 5, "ON" and "OFF" of the sensor power supply respectively indicate supply of power (ON) and the stop of power supply (OFF) with respect to the sensor (the sensor array 501 and a drive circuit 502).

"ON", "low power state", and "OFF" of the amplifier power supply respectively represent supply of power to the amplifier (a sample and hold circuit 503, a multiplexer 504, an A/D converter 511, and an amplifier 510) (ON), supply of power to some components of the amplifier (low power state), and the stop of power supply to the amplifier (OFF). Furthermore, "ON" and "OFF" of the irradiation detection unit power supply respectively indicate supply of power (ON) and the stop of power supply (OFF) with respect to the irradiation detection unit 530.

If the radiation imaging apparatus 101 is in the idle state (step S301), the sensor power supply, amplifier power supply, and irradiation detection power supply are OFF. In the image stabilization waiting state in which the state of the radiation imaging apparatus 101 transits from the idle state (step S301) to the imaging preparation state (step S302), the sensor power supply is ON, the amplifier power supply is in the low power state in which power is supplied to some components of the amplifier, and the irradiation detection unit power supply is OFF. In the image stabilization waiting state, after turning on the sensor power supply, the sensor driving unit 110 performs driving to discard electric charges for initializing the sensor array 501.

In the imaging preparation state (step S302), the sensor power supply is ON, the amplifier power supply is in the low power state in which power is supplied to some components of the amplifier, and the irradiation detection unit power supply is OFF. Also in the imaging preparation state (step S302), the sensor driving unit 110 performs driving to discard electric charges for initializing the sensor array 501.

In the imaging enable state (step S304), the sensor power supply is ON, the amplifier power supply is in the low power state in which power is supplied to some components of the amplifier, and the irradiation detection unit power supply is ON. By turning on the irradiation detection unit power supply, the irradiation detection unit 530 can detect the start of radiation irradiation. Also in the imaging enable state (step S304), the sensor driving unit 110 performs driving to discard electric charges.

In the imaging state, the sensor power supply is ON, and the sensor driving unit 110 controls the driving of the sensor array 501, thereby accumulating electric charges generated by radiation irradiation. In the electric charge accumulation state, the amplifier power supply is in the low power state. When the sensor driving unit 110 performs driving to read out the electric charges, the amplifier power supply is switched from the low power state to a higher power supply state, that is, the ON state.

In the imaging state, the irradiation detection unit power supply is switched from the ON state to the OFF state. As described above, the operating state control unit 116 controls the supply of power to each unit according to the operating state of the radiation imaging apparatus 101, thereby saving the power of the radiation imaging apparatus 101.

Figure 6A:
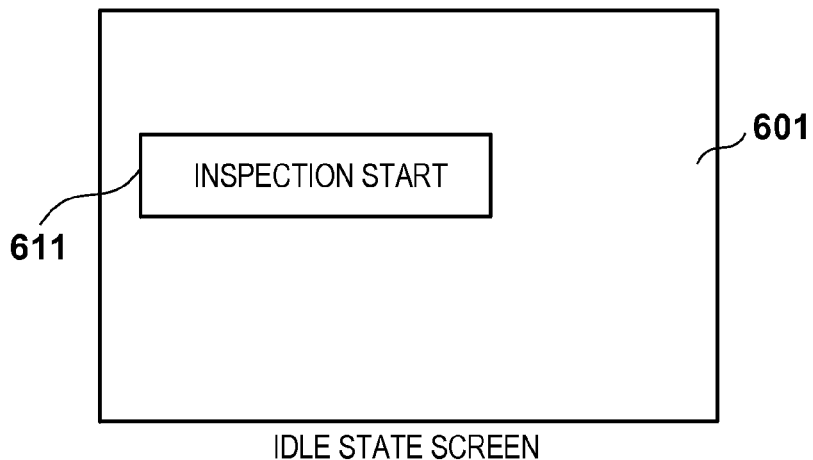
FIGS. 6A to 6E are views each exemplifying the screen of a display unit.
Figure 6B:
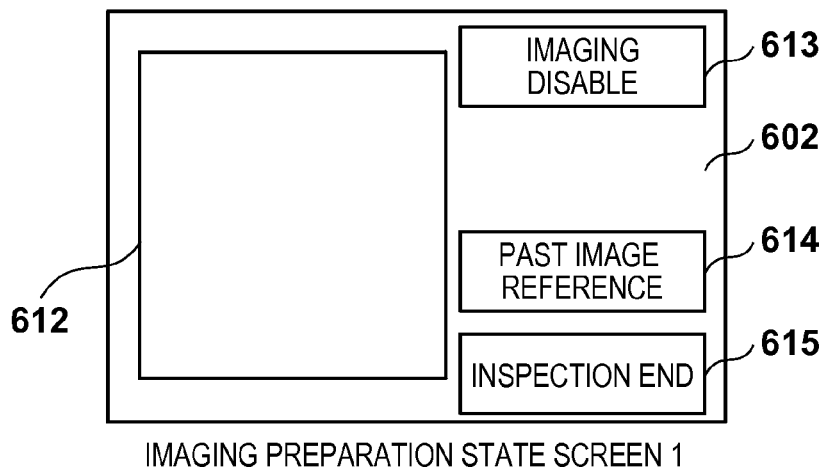

FIGS. 6A to 6E are views each exemplifying the screen of the display unit 124 for instructing the operation of the radiation imaging apparatus 101. The display control unit 123 of the console 102 performs display control of the display unit 124. The display screen shown in FIG. 6A is an idle state screen 601 when the radiation imaging apparatus 101 is in the idle state. When the user (operator) presses an inspection start button 611, the display control unit 123 switches the screen, and the display screen of the display unit 124 transits to an imaging preparation state screen 1 602 (FIG. 6B). Also in the image stabilization waiting state in which the operating state transits from the idle state to the imaging preparation state (FIG. 5), the imaging preparation state screen 1 602 is displayed as a screen displayed to the user (operator). While the imaging preparation state screen 1 602 is displayed, the operating state of the radiation imaging apparatus 101 transits from the idle state to the imaging preparation state through the image stabilization waiting state.

In the imaging preparation state screen 1 602 shown in FIG. 6B, "imaging disable" (imaging preparation state) is displayed in a region 613 indicating the operating state of the radiation imaging apparatus. Furthermore, a past image reference button 614 for referring to images captured in the past and an inspection end button 615 for terminating imaging by the radiation imaging apparatus 101 are displayed. If, for example, the operator presses the past image reference button 614, the display control unit 123 switches the display screen to a past image selection screen for selecting an inspection target patient from a list of patients imaged in the past. The past image selection screen is displayed in a display region 612 shown in FIG. 6B. In the past image selection screen, the operator can refer to the past captured images of the desired inspection target patient, and select a past image. The selected past image is displayed in the display region 612.

When the operator presses the inspection end button 615 in the imaging preparation state screen 1 602 shown in FIG. 6B to stop imaging, the operating state control unit 116 returns the operating state from the imaging preparation state to the idle state. The display control unit 123 switches the screen, and the display screen of the display unit 124 transits to the idle state screen 601. When the radiation imaging apparatus 101 completes preparation for imaging while the imaging preparation state screen 1 602 shown in FIG. 6B is displayed, the operating state control unit 116 switches the operating state from the imaging preparation state to the imaging enable state. The display control unit 123 switches the screen and the display screen of the display unit 124 transits to an imaging enable state screen 603.

Figure 6C:
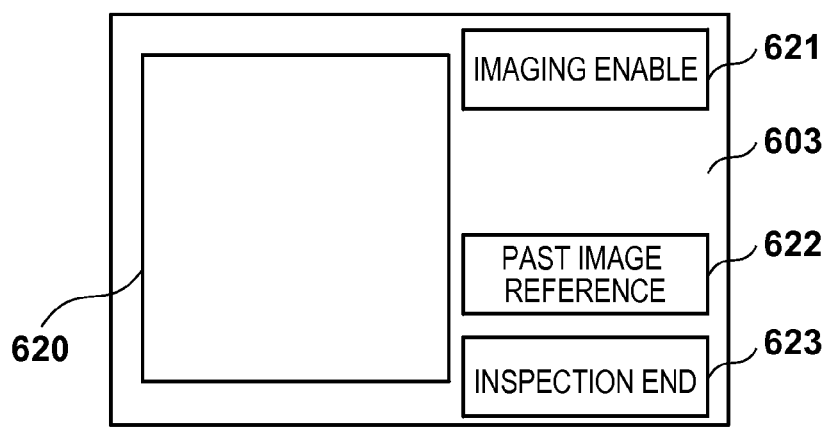

In the imaging enable state screen 603 shown in FIG. 6C, "imaging enable" is displayed in a region 621 indicating the operating state of the radiation imaging apparatus 101. A past image reference button 622 for referring to images captured in the past and an inspection end button 623 for terminating imaging by the radiation imaging apparatus 101 are displayed in the imaging enable state screen 603. When the past image reference button 622 is pressed while the imaging enable state screen 603 shown in FIG. 6C is displayed, the operating state control unit 116 of the radiation imaging apparatus 101 switches the operating state from the imaging enable state to the imaging preparation state. The display control unit 123 switches the screen, and the display screen of the display unit 124 transits to an imaging preparation state screen 2 604 shown in FIG. 6D. The past image selection screen is displayed in a display region 630 shown in FIG. 6D. In the past image selection screen, the operator can refer to the past captured images of a desired inspection target patient, and select a past image. The selected past image is displayed in the display region 630.

Figure 6D:
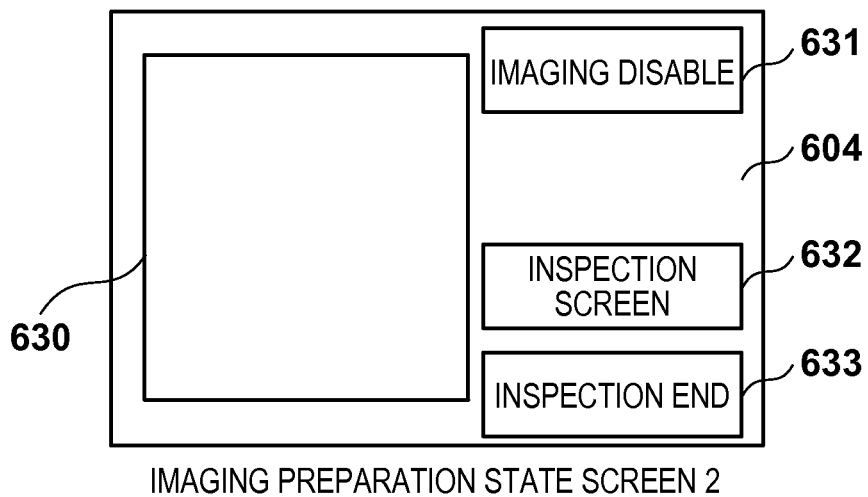

In the imaging preparation state screen 2 604 shown in FIG. 6D, "imaging disable" (imaging preparation state) is displayed in a region 631 indicating the operating state of the radiation imaging apparatus. Furthermore, an inspection screen button 632 and an inspection end button 633 for terminating imaging by the radiation imaging apparatus 101 are displayed. If the operator presses the inspection end button 633 in the imaging preparation state screen 2 604 shown in FIG. 6D to stop imaging, the operating state control unit 116 switches the operating state from the imaging preparation state to the idle state. The display control unit 123 switches the screen and the display screen of the display unit 124 transits to the idle state screen 601. When the operator presses the inspection screen button 632 in the imaging preparation state screen 2 604 shown in FIG. 6D, the operating state control unit 116 switches the operating state from the imaging preparation state to the imaging enable state. The display control unit 123 returns display of the display unit 124 to the imaging enable state screen 603 shown in FIG. 6C which was displayed before switching the screen to that shown in FIG. 6D.

A subject before imaging is displayed in a display region 620 of the imaging enable state screen 603 shown in FIG. 6C. The operator can adjust the state of the subject (for example, an imaging portion and the respiratory timing of the subject) while seeing the image, thereby satisfying conditions required for imaging. When the operator presses a radiation irradiation switch while the imaging enable state screen 603 shown in FIG. 6C is displayed, the radiation generating apparatus 103 performs radiation irradiation. The operating state control unit 116 switches the operating state from the imaging enable state to the imaging state. The display control unit 123 switches the screen and the display screen of the display unit 124 transits to an imaging state screen 605 shown in FIG. 6E, thereby displaying a captured image in a display region 640.

Figure 6E:
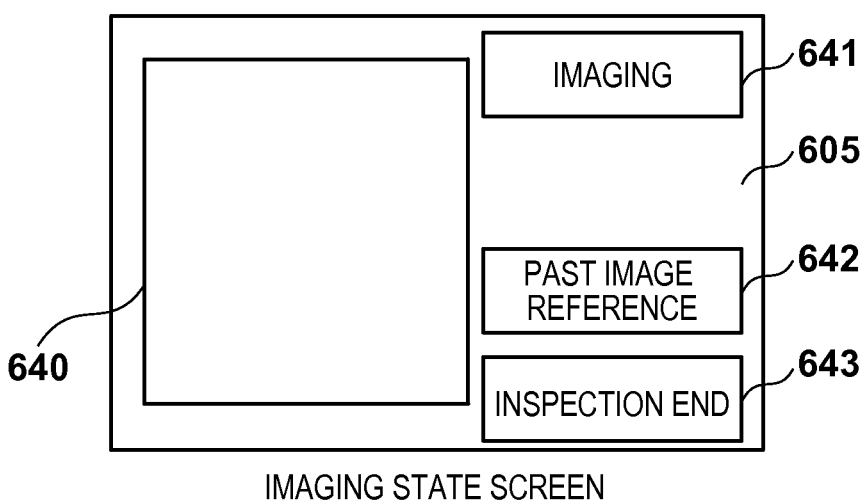

In the imaging state screen 605 shown in FIG. 6E, "imaging" is displayed in a region 641 indicating the operating state of the radiation imaging apparatus. Furthermore, a past image reference button 642 for referring to images captured in the past and an inspection end button 643 for terminating imaging by the radiation imaging apparatus 101 are displayed in the imaging state screen 605. If, for example, the operator presses the past image reference button 642 after imaging, the operating state control unit 116 switches the operating state to the image preparation state. The display control unit 123 switches the screen, and the display screen of the display unit 124 transits to, for example, the imaging preparation state screen 2 604 shown in FIG. 6D. The past image selection screen is displayed in the display region 630 shown in FIG. 6D. When the operator presses the inspection screen button 632 in the imaging preparation state screen 2 604 shown in FIG. 6D, the display control unit 123 returns display of the display unit 124 to the imaging state screen 605 shown in FIG. 6E which was displayed before switching the screen to that shown in FIG. 6D. When the operator presses the inspection end button 615 of the imaging state screen 605 shown in FIG. 6E, the operating state control unit 116 exits the imaging state (imaging). Upon exiting the imaging state, the operating state control unit 116 switches the operating state of the radiation imaging apparatus 101 to the idle state.

According to each of the above-described embodiments, it is possible to control the operating state of the apparatus according to the result of determining whether the remaining imaging enable time is equal to or longer than the threshold time. This allows imaging while ensuring a sufficient imaging time in imaging, thereby preventing desired radiation imaging from failing (misshooting).

A scheme in which no communication is performed between the radiation generating apparatus and the radiation imaging apparatus can reduce the possibility of misshooting by shortening the time until the radiation imaging apparatus enters the imaging enable state to ensure a sufficient imaging time in actual imaging while saving the power.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-044720, filed Mar. 6, 2013, which is hereby incorporated by reference herein in its entirety.

What is claimed is:

1. A control apparatus for a radiation sensor, including pixels each for obtaining electric charges, comprising:
a control unit configured to drive the radiation sensor in an imaging-enable state in which the radiation sensor is capable of executing radiation imaging, and stop driving of the radiation sensor in the imaging-enable state when a first time has elapsed after an initialization operation that initializes the radiation sensor; and
a receiving unit configured to receive, from an external apparatus, an instruction signal for transiting a state of the radiation sensor to the imaging-enable state, wherein the time the instruction signal is received is a second time from the initialization operation, and
wherein the control unit is configured to, in response to reception of the instruction signal, control a state of the radiation sensor based on a difference between the first time and the second time.

2. The apparatus according to claim 1, wherein the radiation sensor includes an array of pixels each including a photoelectric conversion device and a switching element connected to one end of the photoelectric conversion device, and signal lines for reading out electric signals from the photoelectric devices, and
wherein the control unit outputs the electric signals of the pixels via the signal lines by sequentially, selectively setting the switching elements in an ON state for each row, as the driving to start imaging.

3. The apparatus according to claim 1, wherein the radiation sensor includes an array of pixels each including a photoelectric conversion device and a switching element connected to one end of the photoelectric conversion device, signal lines for reading out electric signals from the photoelectric conversion devices, and a detection unit connected to the other end of each of the photoelectric conversion devices and configured to detect radiation irradiation for the radiation sensor, wherein the control unit starts driving to output the electric signals of the pixels via the signal lines by sequentially, selectively setting the switching elements in an ON state for each row, on or after entering the imaging-enable state, and
the detection unit detects radiation irradiation for the radiation sensor based on the electric signals input to the detection unit during execution of the driving to start imaging.

4. The apparatus according to claim 1, wherein
the receiving unit receives, from the external apparatus, a signal output upon pressing of a button for instructing display of a second screen different from a first screen for executing radiation imaging while the first screen is displayed on a display unit, and
the control unit controls the state of the radiation sensor in response to reception of the signal.

5. The apparatus according to claim 1, wherein
the receiving unit receives, from the external apparatus, a signal output upon pressing of a button for instructing display of a second screen different from a first screen for executing radiation imaging while the first screen is displayed on a display unit, and
the control unit stops the driving in response to reception of the signal.

6. The apparatus according to claim 1, wherein
a radiation detection unit includes a photodetection array with a plurality of photoelectric conversion devices, a bias line for supplying a voltage from a bias power supply to each of the plurality of respective photoelectric conversion devices, switching elements respectively connected to the plurality of photoelectric conversion devices, and column signal lines respectively connected to the plurality of photoelectric conversion devices via the switching elements, and
a signal generating unit generates a signal value corresponding to a current flowing through the bias line during a periodic initialization operation, and includes a driving circuit configured to set the switching elements in an OFF state based on the signal value, and a readout circuit configured to obtain radiation image data based on image signals obtained via the column signal lines.

7. The apparatus according to claim 5, wherein the radiation sensor includes an array of pixels each including a photoelectric conversion device and a switching element connected to one end of the photoelectric conversion device, signal lines for reading out electric signals from the photoelectric conversion devices, and a detection unit connected to the other end of each of the photoelectric conversion devices and configured to detect radiation irradiation for the radiation sensor, and
wherein the control unit sets a function of detecting radiation irradiation for the radiation sensor in the imaging-enable state by controlling the detection unit in response to reception of the instruction signal.

8. A radiation imaging apparatus comprising:
a radiation sensor including pixels each for obtaining electric charges;
a control unit configured to drive the radiation sensor in an imaging-enable state in which the radiation sensor is capable of executing radiation imaging, and stop driving of the radiation sensor in the imaging-enable state when a first time has elapsed after an initialization operation that initializes the radiation sensor; and
a receiving unit configured to receive, from an external apparatus, an instruction signal for transiting a state of the radiation sensor to the imaging-enable state, wherein the time the instruction signal is received is a second time from the initialization operation, and wherein the control unit is configured to, in response to reception of the instruction signal, control a state of the radiation sensor based on a difference between the first time and the second time.

9. A radiation imaging system comprising:
a radiation imaging apparatus according to claim 8; and
a console configured to receive a radiation image obtained from the radiation imaging apparatus.

10. The apparatus according to claim 8, further comprising a radiation generating unit.

11. A control apparatus for a radiation sensor, including pixels each for obtaining electric charges, comprising:
a control unit configured to drive the radiation sensor in an imaging-enable state in which the radiation sensor is capable of executing radiation imaging, and stop driving of the radiation sensor in the imaging-enable state when a first time has elapsed after an initialization operation that initializes the radiation sensor; and
a receiving unit configured to receive, from an external apparatus, an instruction signal for transiting a state of the radiation sensor to the imaging-enable state, wherein the time the instruction signal is received is a second time from the initialization operation, and
wherein the control unit is configured to, in response to reception of the instruction signal, control a state of the radiation sensor based on the first time and the second time.

12. The control apparatus according to claim 11, wherein the control unit controls the state of the radiation sensor based on a comparison between a predetermined threshold time and a difference between the first time and the second time.

13. The apparatus according to claim 11, wherein the radiation sensor includes an array of pixels each including a photoelectric conversion device and a switching element connected to one end of the photoelectric conversion device, and signal lines for reading out electric signals from the photoelectric devices, and
wherein the control unit outputs the electric signals of the pixels via the signal lines by sequentially, selectively setting the switching elements in an ON state for each row, as the driving to start imaging.

14. The apparatus according to claim 11, wherein the radiation sensor includes an array of pixels each including a photoelectric conversion device and a switching element connected to one end of the photoelectric conversion device, signal lines for reading out electric signals from the photoelectric conversion devices, and a detection unit connected to the other end of each of the photoelectric conversion devices and configured to detect radiation irradiation for the radiation sensor,
wherein the control unit starts driving to output the electric signals of the pixels via the signal lines by sequentially, selectively setting the switching elements in an ON state for each row, on or after entering the imaging-enable state, and
wherein the detection unit detects radiation irradiation for the radiation sensor based on the electric signals input to the detection unit during execution of the driving to start imaging.

15. The apparatus according to claim 11, wherein the receiving unit receives, from the external apparatus, a signal output upon pressing of a button for instructing display of a second screen different from a first screen for executing radiation imaging while the first screen is displayed on a display unit, and
wherein the control unit controls the state of the radiation sensor in response to reception of the signal.

16. The apparatus according to claim 11, wherein the receiving unit receives, from the external apparatus, a signal output upon pressing of a button for instructing display of a second screen different from a first screen for executing radiation imaging while the first screen is displayed on a display unit, and
wherein the control unit stops the driving in response to reception of the signal.

17. The apparatus according to claim 16, wherein the radiation sensor includes an array of pixels each including a photoelectric conversion device and a switching element connected to one end of the photoelectric conversion device, signal lines for reading out electric signals from the photoelectric conversion devices, and a detection unit connected to the other end of each of the photoelectric conversion devices and configured to detect radiation irradiation for the radiation sensor, and
wherein the control unit sets a function of detecting radiation irradiation for the radiation sensor in the imaging-enable state by controlling the detection unit in response to reception of the instruction signal.

18. The apparatus according to claim 11, wherein a radiation detection unit includes a photodetection array with a plurality of photoelectric conversion devices, a bias line for supplying a voltage from a bias power supply to each of the plurality of respective photoelectric conversion devices, switching elements respectively connected to the plurality of photoelectric conversion devices, and column signal lines respectively connected to the plurality of photoelectric conversion devices via the switching elements, and
wherein a signal generating unit generates a signal value corresponding to a current flowing through the bias line during a periodic initialization operation, and includes a driving circuit configured to set the switching elements in an OFF state based on the signal value, and a readout circuit configured to obtain radiation image data based on image signals obtained via the column signal lines.

19. A radiation imaging apparatus comprising:
a radiation sensor including pixels each for obtaining electric charges;
a control unit configured to drive the radiation sensor in an imaging-enable state in which the radiation sensor is capable of executing radiation imaging, and stop driving of the radiation sensor in the imaging-enable state when a first time has elapsed after an initialization operation that initializes the radiation sensor; and
a receiving unit configured to receive, from an external apparatus, an instruction signal for transiting a state of the radiation sensor to the imaging-enable state, wherein the time the instruction signal is received is a second time from the initialization operation, and
wherein the control unit is configured to, in response to reception of the instruction signal, control a state of the radiation sensor based on the first time and the second time.

20. A radiation imaging system comprising:
a radiation imaging apparatus according to claim 19; and
a console configured to receive a radiation image obtained from the radiation imaging apparatus.

* * * * *